Figure 1:
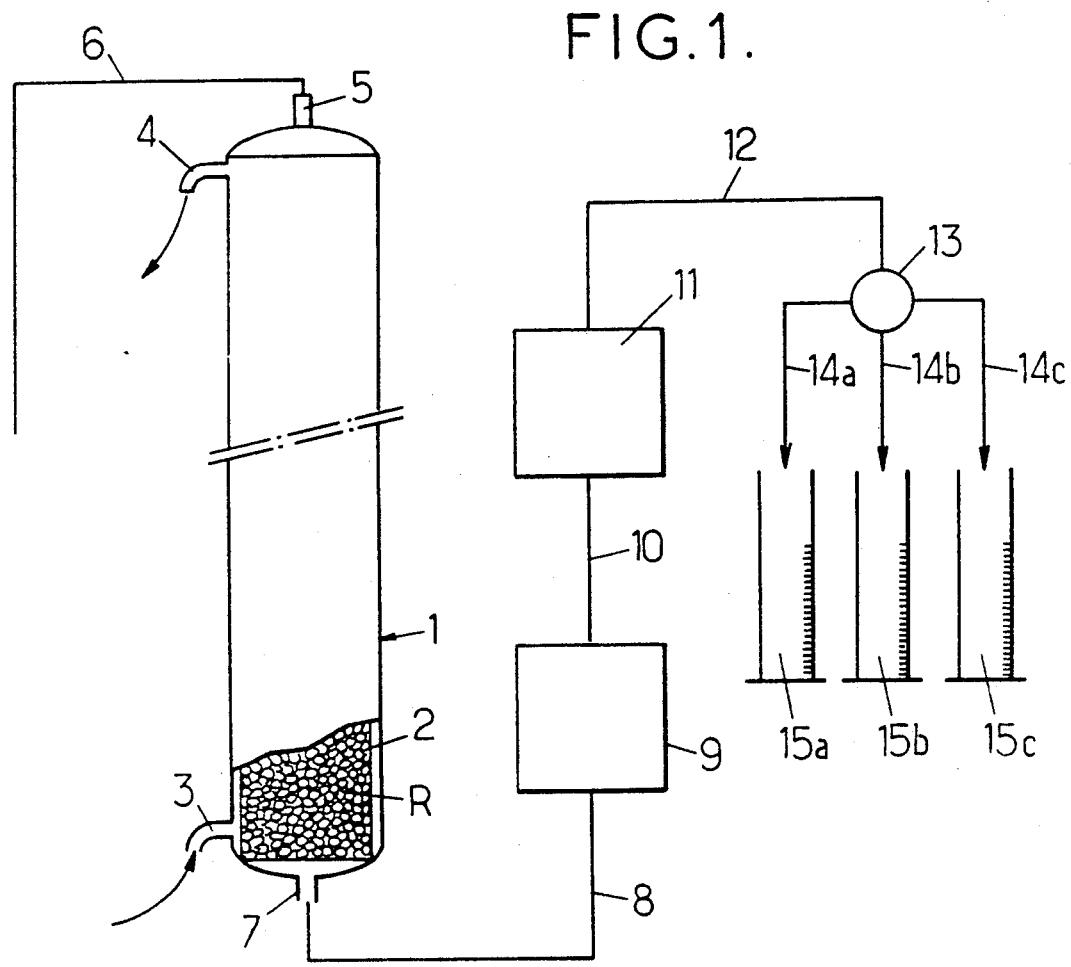

United States Patent [19]

Duflot et al.

[11] Patent Number: 5,032,686

[45] Date of Patent: Jul. 16, 1991

[54] METHOD FOR THE RECOVERY OF CITRIC ACID FROM A LIQUOR CONTAINING THE SAME

[75] Inventors: Pierrick Duflot; Jean-Bernard Leleu, both of Lestrem, France

[73] Assignee: Roquette Freres, Lestrem, France

[21] Appl. No.: 361,043

[22] Filed: Jun. 5, 1989

[30] Foreign Application Priority Data

Jun. 6, 1988 [FR] France ............................ 88 07505

[51] Int. Cl.$^5$ ............................................ C67C 51/42
[52] U.S. Cl. .................................. 562/580; 562/584
[58] Field of Search ............................ 562/580, 584

[56] References Cited

U.S. PATENT DOCUMENTS 4,288,619 9/1981 Devos et al. ..................... 562/580
4,720,579 1/1988 Kulprathipanja ................ 562/580

FOREIGN PATENT DOCUMENTS 688245 6/1964 Canada ............................. 562/580
4313967 6/1968 Japan ................................ 562/580
868926 5/1961 United Kingdom ............. 562/580

OTHER PUBLICATIONS

Chemical Abstracts, vol. 90, No. 21, May 21, 1979, p. 447, No. 168073h, Columbus, Ohio, U.S.

Primary Examiner—Bruce Gray
Attorney, Agent, or Firm—Larson and Taylor

[57] ABSTRACT

Method for the recovery of citric acid from a liquor containing the same, wherein successively, in a first step, the liquor containing the citric acid is put into contact with a cationic resin in the hydrogen form during a duration sufficient to reach an optimal adsorption of the citric acid, in a second step, the resin is treated by means of an elution agent and the fraction of eluate rich in purified citric acid is recovered.

15 Claims, 2 Drawing Sheets

METHOD FOR THE RECOVERY OF CITRIC ACID FROM A LIQUOR CONTAINING THE SAME

The invention relates to a method for the recovery of citric acid from a liquor containing the same.

The expression "liquor" denotes fermentation liquors as well as the mother-waters or mother-liquors from the fermentation of citric acid.

It is already known to prepare citric acid by crystallization from syrups sufficiently rich in that product and sufficiently concentrated.

It is also known to prepare the syrups concerned from fermentation liquors.

In that respect, it is usual to treat with lime fermentation liquors previously deprived of the mycelium they contain and to recover then by filtration the insoluble calcium citrate thus produced due to which any soluble impurities are removed; the thus produced calcium citrate is decomposed under the action of sulfuric acid, thus setting free the citric acid. The calcium sulphate which is produced during that reaction is separated by filtration; the residual cations are eliminated by passing the filtrate which contains the citric acid on a ion exchange resin working in the hydrogen cycle under conditions such that only the cations are adsorbed.

That method which permits elimination of mineral and organic soluble impurities present in the fermentation liquors and which provides with a good yield solutions sufficiently rich in citric acid for the crystallization of the latter, presents the major drawbacks of consuming important quantities of sulfuric acid and of providing important quantities of calcium sulphate which is a polluting product neither able to be recycled nor to be reused.

In order to overcome these drawbacks, those skilled in the art tried to provide other methods which would be able to partially eliminate the impurities contained in the liquors of fermentation of citric acid.

Most of these methods are based on extraction with organic solvents of the citric acid contained in the said liquors. For several reasons, these methods were not entirely satisfying and had never reached an industrial exploitation.

Other purification methods, adapted to separate the major part of the impurities constituted by high molecular weight particles, are based on the use of
- either reverse osmosis filtration membranes or ultra-filtration which exclude the said high molecular weight molecules,
- or non ionic adsorbent resins which adsorb the said impurities.

However, the adsorbent resins must be regenerated after each adsorption cycle by means of alcali and of organic solvents.

Moreover, in both cases, the low molecular weight ionic impurities which were not separated from the citric acid and which consist above all of mineral cations and anions, are eliminated by passing the liquors over cationic and anionic resins under conditions such that, as far as the cationic resins are concerned, only the cations and, as far as the anionic resins are concerned, only the anions of strong mineral acids are adsorbed, realizing thus a purification by ion exchange. When the said resins are saturated, the adsorbed impurities are eluted, the said elution being carried out, as far as the cationic resin is concerned, by means of a strong acid solution, generally of hydrochloric acid and, as far as the anionic resin is concerned, by means of a solution of a strong base, generally natrium hydroxide, in order to regenerate the said resins and to make them adapted for a further ion exchange purification cycle.

These methods are consequently very expensive and difficult to carry out and were not developed on an industrial scale.

As none of the known methods was entirely satisfying, the Applicants tried to find a method adapted to permit the recovery of citric acid from fermentation liquors or from crystallization mother-liquors containing the latter, without using sulfuric acid or organic solvents, said method being moreover simple and economic to carry out.

And the method which they had the merit to find is characterized by the fact that, successively,
- in a first step, the liquor containing the citric acid is put into contact with a cationic resin in the hydrogen form during a duration sufficient to reach an optimal adsorption of the citric acid,
- in a second step, the resin is treated by means of an elution agent and the fraction of eluate rich in purified citric acid is recovered.

The raw material subjected to citric fermentation is generally constituted by molasses but it is also possible to use pure carbon hydrates and, in that latter case, the citric fermentation authorizes obtaining liquors which are sufficiently poor in impurities to permit at least a first crystallization of citric acid without purification, only the crystallization mother-liquors being then treated according to the invention in a way to extract a second or a third crop of crystallized acid.

Preferably, the liquor which is put into contact with the resin is warm, its temperature being advantageously from 50° to 95° C. and still more preferably comprised between 65° and 80° C.

According to an advantageous embodiment of the method according to the invention, the elution agent is consisting of water; the temperature of the said water is higher than 40° C., preferably from 50° to 95° C. and, still more preferably, close to the temperature of the liquor being treated.

According to another advantageous embodiment of the method according to the invention, the resin which is implemented has a low granulometry and a low rate of reticulation with divinylbenzene, cationic resins of the styrene-divinylbenzene type being preferred.

The rate of reticulation of the said resins is generally comprised between 5 and 10%, preferably between 4 and 8% and their granulometry is comprised between 0.1 and 1 mm, preferably between 0.2 and 0.6 mm.

In order to obtain an optimal adsorption of the citric acid, that is to say an adsorption of a proportion of at least about 90% of the total amount of citric acid contained in the liquor, a given fraction of the said liquor should remain in contact with the resin from 20 minutes to 10 hours, preferably from 1 h to 3 h ½; in practice, the said duration corresponds to a delivery per hour of 0.1 volume to 3 volumes, preferably from 0.3 volume to 1 volume per volume of resin.

Figure 2:
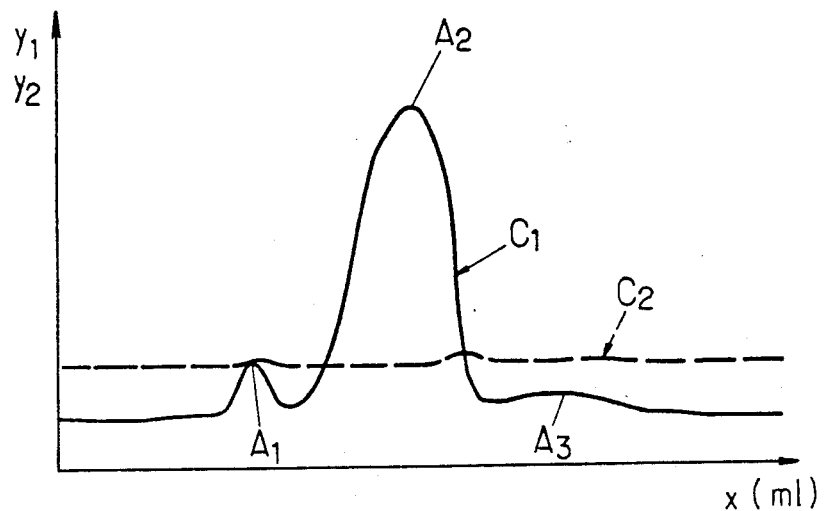
Figure 3:
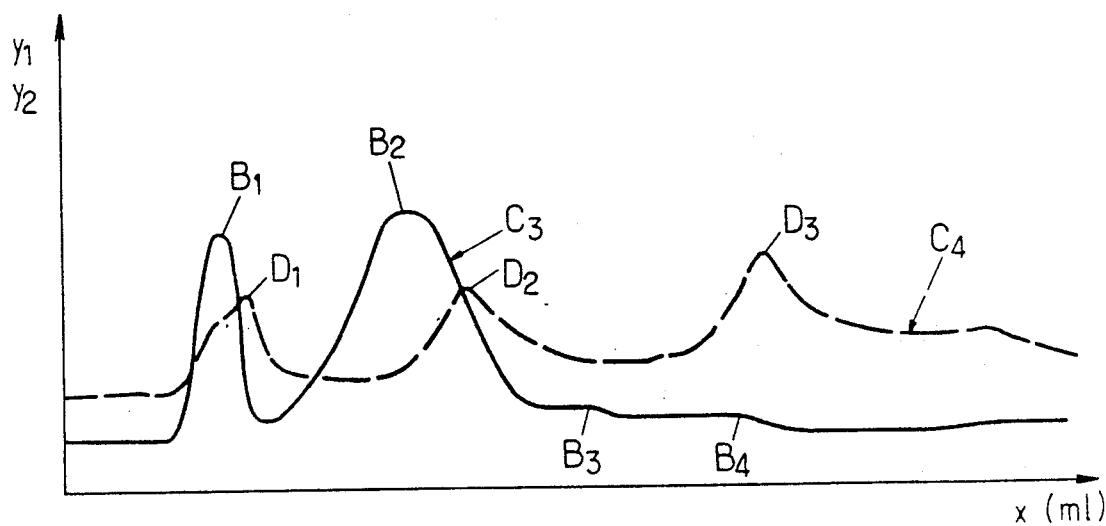

The invention also contemplates other features which will be disclosed hereinafter and it will be, in any case, well understood by means of the following description and the non limitative examples which relate to advantageous embodiments, the said description and examples being illustrated by the drawings in which FIG. 1 is a schematic representation of an installation adapted to carry out the method according to the invention and FIGS. 2 and 3 show curves representing the evolution of the said method.

The fermentation liquor or the crystallization mother-liquors whose dry matter content is generally from 10 to 75% by weight and, in particular, close to 50% by weight and which contains for the major part the citric acid under its free form, is first put into contact with a cationic resin in the hydrogen form under conditions such that the totality of the cations of the raw material be replaced by protons. That permutation, despite the fact that it is not compulsory, presents the advantage of protecting the evaporators from the formation of incrusting deposits, thus providing the adsorption resins with a longer life.

Then, the liquor to be purified is put into contact with the selected resin, which may be for instance selected from those of the group comprising the hereafter indicated resins which are identified by their trademark:

TSW40 marketed by BAYER,

C204 marketed by DUOLITE,

DIAION SKlBS marketed by MITSUBISHI,

CFX4 marketed by SYBRON.

In that respect, the resin is advantageously put into columns comprising a thermostating jacket. The said jacketing of the columns is not necessary when the dimensions of the installation are such that the thermic losses do no longer constitute a major drawback.

The selected duration of contact is the one necessary to realize an optimal adsorption of the citric acid.

Then, the resin is eluted. In that respect, it is possible to use water preferably warm, having a temperature close to the temperature of the raw material; generally, that temperature is comprised between 50° and 95° C.

In practice, the elution rate is from 0.1 volume to 3 volumes, preferably from 0.3 volume to 1 volume, of elution agent per volume of resin and per hour.

The eluted fractions are recollected according to aliquote parts.

It is noticed that, unexpectedly and surprisingly, the first eluted fractions essentially contain high molecular weight products as well as mineral anions and sugars which were not fermented, i.e. especially saccharose, maltose, isomaltose and others, the subsequent fractions contain the citric acid which has a very high purity and the last fractions contain various organic acids such as gluconic acid, oxalic acid and others as well as other compounds which adsorb strongly on the resin such as betaine, compounds which were provided by constituent elements of the culture medium or which were synthesized during the fermentation at the same time as the citric acid.

The fractions which contain the citric acid are concentrated to a dry matter content sufficient for the crystallization of the citric acid, that is to say higher than about 60% by weight, the crystallized citric acid being then separated by filtration.

The method according to the invention provides a almost perfect separation of the citric acid from the impurities contained in the liquors, that result being obtained without consumption of chemical products and without formation of polluting by-products.

In order to carry out the method according to the invention, it is possible to use one or several chromatographic columns which are serially or parallelly connected and which work continuously or discontinuously; these columns must be equipped with means adapted to feed them with raw material and with elution agent and they must also be equipped with means adapted to collect the successive fractions of eluate.

By way of illustration, FIG. 1 shows an installation comprising a single column working discontinuously. Distinctly higher performances can be obtained by means of installations comprising several columns working continuously, especially of the type disclosed in the French Patent specification No. 79 10564; the performances of the said installations are represented by the amount of dry matter of purified liquor per volume of resin and per unit of time as well as by the dry matter content of the various fractions containing the purified citric acid, on the one hand, and the impurities, on the other hand; now, it should be noticed that the richness of the various fractions which are separated is identical whatever the installation used.

The installation comprising a single column as represented in FIG. 1 comprises a glass column 1 equipped with a jacket 2 and having a capacity of 350 ml, a diameter of about 1.5 cm and a height of 2 m; it is filled with 339 ml of strong cationic resin, shown by R, for instance the resin marketed under the trademark "C204" by DUOLITE, reticulated with 8% divinylbenzene. The jacket of the said column is provided with thermostated water by means of a pipe 3, the said water being drawn off by means of a pipe 4 in such a way that the temperature of the resin is maintained at 75° C.

The resin is put in its acid or hydrogen form by percolation of 1000 ml of a 1.2N aqueous solution of hydrochloric acid; in order to perform that percolation, the hydrochloric acid is brought to the upper end of the column, i.e. to a pipe 5 by a piping 6; rinsing water is subsequently transported by the same piping. The percolation and the rinsing are carried out with a rate of about 2 volumes of liquid per volume of resin and per hour. For the rinsing, 2000 l of water are used. The liquids immerge from the column by a pipe 7.

Pipe 7 is connected by a piping 8 to a differential refractometer 9 enabling the measuring of the refraction index of the liquid immerging from the column and, thus, the detection of the presence of soluble matters and their quantification, the said refractometer being itself connected by a piping 10 to a UV detector shown in 11, working at 280 nm in order to detect the nitrogenous matters; refractometer 9 and detector 11 are connected serially.

Detector 11 is connected by a piping 12 to a four ways cock 13 adapted to conduct by means of pipes 14a, 14b and 14c the eluate transported by the piping 12 into three graduated vessels respectively 15a, 15b and 15c.

After permutation under acid form of the resin contained in the column, a certain amount of fermentation liquor is injected at the top of the said column, the said liquor being then eluated by means of warm water.

The indications provided by the UV detector 11 and by the refractometer 9 allow to separate the eluate at the exit of the column into three fractions containing respectively:

the excluded impurities,
the purified citric acid, the adsorbed impurities,
the said three fractions being respectively introduced into the vessels 15a, 15b and 15c.

EXAMPLE 1

Recovery of citric acid from a fermentation liquor obtained by fermentation of a medium on the basis of starch hydrolysate The liquor treated presents a richness in citric acid of 89.3% by weight with respect to the dry matter and contains organic and mineral impurities among which 1.1% of gluconic acid, 0.5% of oxalic acid, 2% of maltose and about 2% of sulphated ashes; the said liquor was filtered and concentrated to a dry matter content of 50%; its density is 1.22 g/ml.

1 ml of the said liquor is introduced at the upper extremity of the column of resin hereabove described and illustrated by FIG. 1.

The elution is carried out by means of warm water with a rate of 152 ml/hour; the temperature of the jacketing is maintained at 75° C.

The eluate begins to appear at the outlet of the column after about 42 minutes. The variation of its dry matter content with respect to the quantity x, expressed in ml, of recovered eluate, is materialized by a curve $C_1$ representing on the diagram of FIG. 2 the variation y1 (arbitrary scale) of the refractometric lecture (refractometer 9) in function of x.

Curve $C_1$ comprises 3 peaks identified by the letters $A_1$, $A_2$ and $A_3$.

Peak $A_1$ corresponds to a first fraction containing the excluded impurities and represents a volume of 16 ml. That first fraction of eluate is recollected in the vessel 15a into which it is conducted by a piping 14a by means of the cock 13.

Peak $A_2$ represents a volume of 43 ml and corresponds to a second fraction which contains the purified citric acid, fraction which is recollected in the vessel 15b by handling of cock 13 conducting the said fraction by means of the piping 14b.

Peak $A_3$ represents a volume of 36 ml and corresponds to a third fraction which contains the impurities which are stronger adsorbed than the citric acid; that fraction is recollected in vessel 15c by means of a new handling of cock 13 conducting the eluate by way of piping 14c.

The variation y2 of the optical density (arbitrary scale) at 280 nm of the eluate, still in function of the quantity x of recollected eluate, measured by the detector 11, is materialized by a curve $C_2$ shown on the diagram of FIG. 2.

Curve $C_2$ is practically flat during the whole duration of the elution and does not provide, in that case, elements permitting the evaluation of the efficiency of the purification. That is due to the fact that the raw materials composing the fermentation liquors were very pure (starch hydrolysate) and did not comprise substances absorbing UV rays.

In Table I, are recorded the values of the whole dry matter content and of the proportion of citric acid for the three fractions corresponding to the peaks $A_1$, $A_2$ and $A_3$.

TABLE I

| | Total dry matter content (in mg) | Proportion of citric acid (in %) |
| --- | --- | --- |
| Fraction corresponding to peak $A_1$ | 31 | 5 |
| Fraction corresponding to peak $A_2$ | 534 | 99 |
| Fraction corresponding to peak $A_3$ | 45 | 5 |

From the values recorded in Table I, it results that fraction B corresponding to peak $A_2$ contains 97% of the citric acid present in the liquor subjected to the purification, its richness in citric acid being 99%.

EXAMPLE 2

Recovery of citric acid from a fermentation liquor obtained by fermentation of a medium based on molasses The liquor under treatment presents a richness in citric acid of 63.5% by weight with respect to the dry matter and contains organic and mineral impurities among which 6.5% of gluconic acid, 0.3% of oxalic acid, 1.2% of fructose, 3.5% of glucose, 6.6% of dissacharides and 13.5% of sulphated ashes; that liquor had been filtered and presents a dry matter content of 16.5%; its density is 1.07 g/ml.

An amount of 2 ml of that liquor is introduced at the top of the column of resin disclosed hereabove and illustrated by FIG. 1.

The elution is carried out by means of warm water with a rate of 162 ml/hour; the temperature of the jacketing is maintained at 75° C.

The eluate begins to appear at the outlet of the column after about 42 minutes. The variation of its dry matter content in function of the quantity x, expressed in ml, of recovered eluate, is materialized by a curve $C_3$ representing on the diagram of FIG. 3 the variation y1 (arbitrary scale) of the refractometric lecture (refractometer 9) in function of x.

$C_3$ comprises 4 peaks identified by the letter $B_1$, $B_2$, $B_3$ and $B_4$.

Peak $B_1$ corresponds to a first fraction containing the excluded impurities and represents a volume of 22 ml. That first fraction of eluate is recollected in the vessel 15a into which it is conducted by a piping 14a by means of the cock 13.

Peak $B_2$ represents a volume of 59 ml and corresponds to a second fraction which contains the purified citric acid, that fraction being recollected in the vessel 15b by handling of cock 13 conducting the said fraction by means of the piping 14b.

Peak $B_3$ and $B_4$ represent a volume of 54 ml and correspond to a third fraction which contains impurities stronger adsorbed than the citric acid; that fraction is recollected in the vessel 15c by a new handling of cock 13 conveying the eluate by means of piping 14c.

The variation y2 of the optical density (arbitrary scale) at 280 nm of the eluate, still in function of the quantity x of recollected eluate, measured by the detector 11, is represented by the curve $C_4$ on the diagram of FIG. 3.

That curve comprises three peaks $D_1$, $D_2$ and $D_3$ representing the impurities contained in the molasses and it is noticed that these impurities, revealed by the peaks $D_1$ and $D_3$, are found again in totality in fractions $B_1$ and $B_3=B_4$ as well as part of the impurities, the presence of which is revealed by peak $D_2$.

It follows that even on liquors whose citric acid content was relatively low, the method according to the invention authorizes obtention of citric acid having a high purity with an excellent yield. The values found for the total dry matter content and the proportion of citric acid in the case of the said three fractions are recorded in Table II.

TABLE II

|  | Total dry matter content (in mg) | Proportion of citric acid (in %) |
|---|---|---|
| Fraction corresponding to peak $B_1$ | 84 | 8 |
| Fraction corresponding to peak $B_2$ | 215 | 98 |
| Fraction corresponding to peak $B_3$ | 54 | 13 |

It appears from the examination of Table II that the fraction corresponding to peak $B_2$ contains 94% of the citric acid present in the liquor subjected to the purification; the richness of the said fraction in citric acid is 98%.

It follows that the method according to the invention for recovering citric acid from fermentation liquors, method whose features sufficiently appear from the preceding description presents, with respect to the already known methods, numerous advantages among which

- the advantage of permitting the recovery of highly purified citric acid by a single chromatographic treatment of a liquor of fermentation of citric acid or of mother-liquors of such a liquor of which a first crop of the said acid has already been separated by crystallization,
- the advantage of not consuming chemical reactances,
- the advantage of not generating polluting products,
- the advantage of using materials (resins) whose stability and the harmlessness are well known,
- the advantage consisting in the possibility to be carried out in installations whose robustness and whose working qualities were proved by the intensive use to which they were subjected in connected with other uses.

We claim:

1. Method for the recovery of citric acid from a liquor containing the same, wherein successively,
   in a first step, the liquor containing the citric acid is put into contact with a cationic resin in the hydrogen form during a duration sufficient to adsorb a proportion of at least 90% of the total amount of the citric acid contained in the liquor,
   in a second step, the resin is treated by means of an elution agent and the fraction of eluate rich in purified citric acid is recovered.

2. Method according to claim 1, wherein the elution agent is water.

3. Method according to claim 1, wherein the elution agent is consisting of water having a temperature higher than 40° C.

4. Method according to claim 1, wherein the elution agent is consisting of water having a temperature comprised between 50° and 95° C.

5. Method according to claim 1, wherein the temperature of the liquor put into contact with the resins is from 50° to 95° C.

6. Method according to claim 1, wherein the temperature of the liquor put into contact with the resins is from 65° to 80° C.

7. Method according to claim 1, wherein the temperature of the liquor put into contact with the resins is from 50° to 95° C. and wherein the temperature of the elution agent is close to the temperature of the liquor.

8. Method according to claim 1, wherein the temperature of the liquor put into contact with the resins is from 65° to 80° C. and wherein the temperature of the elution agent is close to the temperature of the liquor.

9. Method according to claim 1, wherein the resin which is implemented has a low granulometry and a low rate of reticulation with divinylbenzene, the rate of reticulation of the said resins being comprised between 5 and 10% and their granulometry being comprised between 0.1 and 1 mm.

10. Method according to claim 1, wherein the resin which is implemented has a low granulometry and a low rate of reticulation with divinylbenzene, the rate of reticulation of the said resins being comprised between 4 and 8% and their granulometry being comprised between 0.2 and 0.6 mm.

11. Method according to claim 1, wherein the resin which is implemented is consisting of a cationic resin of the styrene-divinylbenzene type, the said resin having a rate of reticulation comprised between 5 and 10% and its granulometry is comprised between 0.1 and 1 mm.

12. Method according to claim 1, wherein the resin which is implemented is consisting of a cationic resin of the styrene-divinylbenzene type, the said resin having a rate of reticulation comprised between 4 and 8% and its granulometry is comprised between 0.2 and 0.6 mm.

13. Method according to claim 1, wherein a given fraction of the said liquor is maintained in contact with the resin from 20 minutes to 10 hours, which corresponds to a delivery per hour of 0.1 volume to 3 volumes per volume of resin.

14. Method according to claim 1, wherein a given fraction of the said liquor is maintained in contact with the resin from 1 h to 3 h ½, which corresponds to a delivery per hour of 0.3 volume to 1 volume per volume of resin.

15. Method according to claim 1, wherein the liquor is obtained from molasses or from carbon hydrates.

* * * * *